(12) United States Patent
Sekhavat et al.

(10) Patent No.: US 12,268,635 B2
(45) Date of Patent: Apr. 8, 2025

(54) GLAUCOMA SHUNTS AND RELATED METHODS OF USE

(71) Applicant: Hexiris Inc., Dieppe (CA)

(72) Inventors: Houfar Sekhavat, Dieppe (CA); Nir Shoham-Hazon, Miramichi (CA)

(73) Assignee: Hexiris Inc., Dieppe (CA)

( * ) Notice: Subject to any disclaimer, the term of this patent is extended or adjusted under 35 U.S.C. 154(b) by 0 days.

(21) Appl. No.: 17/768,184

(22) PCT Filed: Oct. 9, 2020

(86) PCT No.: PCT/CA2020/051358
§ 371 (c)(1),
(2) Date: Apr. 11, 2022

(87) PCT Pub. No.: WO2021/068078
PCT Pub. Date: Apr. 15, 2021

(65) Prior Publication Data
US 2024/0122754 A1    Apr. 18, 2024

(30) Foreign Application Priority Data
Oct. 11, 2019  (CA) ..................................... 3058571

(51) Int. Cl.
*A61F 9/007*          (2006.01)
(52) U.S. Cl.
CPC ...... *A61F 9/00781* (2013.01); *A61F 9/00736* (2013.01)

(58) Field of Classification Search
CPC .............. A61F 9/00781; A61F 9/00736; A61F 2250/0067; A61F 9/0017; A61F 2/82; A61F 2230/0069; A61M 27/002; A61M 27/00
See application file for complete search history.

(56) References Cited

U.S. PATENT DOCUMENTS

| | | | |
|---|---|---|---|
| 5,092,837 A | | 3/1992 | Ritch et al. |
| 5,573,542 A | * | 11/1996 | Stevens ............ A61B 17/12013 223/102 |
| 5,807,302 A | | 9/1998 | Wandel |
| 5,865,831 A | * | 2/1999 | Cozean ............... A61F 9/00802 606/6 |
| 6,007,511 A | * | 12/1999 | Prywes ............... A61F 9/00781 604/9 |
| 6,251,118 B1 | * | 6/2001 | Proudfoot ............... A61F 2/147 606/166 |

(Continued)

OTHER PUBLICATIONS

International Search Report for PCT/CA2020/051358 dated Jan. 18, 2021.

(Continued)

*Primary Examiner* — Adam Marcetich
(74) *Attorney, Agent, or Firm* — MARSHALL, GERSTEIN & BORUN LLP

(57) ABSTRACT

Glaucoma shunts comprising an elongate body with an outer surface and an inner surface, the elongate body comprising an inner wall that defines a lumen spanning a length of the elongate body are disclosed herein. Also disclosed are methods of decreasing intraocular pressure in an eye, the method comprising inserting at least a portion of a glaucoma shunt into an anterior chamber of the eye, and draining aqueous humour from the anterior chamber through the lumen.

17 Claims, 4 Drawing Sheets

(56) References Cited

U.S. PATENT DOCUMENTS

| | | | |
|---|---|---|---|
| 2002/0111603 A1* | 8/2002 | Cheikh | A61K 38/31 |
| | | | 424/422 |
| 2004/0138525 A1* | 7/2004 | Saadat | A61B 1/0055 |
| | | | 600/104 |
| 2005/0010244 A1* | 1/2005 | Melles | A61F 9/007 |
| | | | 606/166 |
| 2005/0119737 A1 | 6/2005 | Bene et al. | |
| 2005/0154412 A1* | 7/2005 | Krueger | A61B 17/24 |
| | | | 606/185 |
| 2005/0266047 A1 | 12/2005 | Tu et al. | |
| 2005/0271704 A1* | 12/2005 | Tu | A61M 27/002 |
| | | | 623/5.13 |
| 2008/0108933 A1* | 5/2008 | Yu | A61L 31/045 |
| | | | 427/2.25 |
| 2008/0228127 A1* | 9/2008 | Burns | A61F 9/00781 |
| | | | 604/9 |
| 2009/0043242 A1* | 2/2009 | Bene | A61F 9/00781 |
| | | | 606/108 |
| 2009/0182421 A1* | 7/2009 | Silvestrini | A61F 9/00781 |
| | | | 623/6.14 |
| 2011/0152838 A1* | 6/2011 | Xia | A61M 11/06 |
| | | | 604/514 |
| 2012/0089073 A1 | 4/2012 | Cunningham, Jr. | |
| 2013/0035551 A1* | 2/2013 | Yu | A61B 1/0052 |
| | | | 600/141 |
| 2013/0150770 A1* | 6/2013 | Horvath | A61F 9/00763 |
| | | | 604/8 |
| 2015/0133946 A1* | 5/2015 | Horvath | A61M 5/3286 |
| | | | 606/108 |
| 2016/0058615 A1 | 3/2016 | Camras et al. | |
| 2016/0287438 A1* | 10/2016 | Badawi | A61K 33/14 |
| 2016/0354309 A1* | 12/2016 | Heitzmann | A61P 27/02 |
| 2017/0056602 A1* | 3/2017 | Medina | A61B 17/24 |
| 2017/0348150 A1* | 12/2017 | Horvath | A61F 9/00781 |
| 2019/0038462 A1* | 2/2019 | Vandiest | A61B 90/39 |
| 2019/0151150 A1 | 5/2019 | Pinchuk et al. | |
| 2019/0274881 A1* | 9/2019 | Romoda | A61F 9/00781 |
| 2019/0357768 A1* | 11/2019 | Shareef | A61B 3/117 |
| 2022/0096271 A1* | 3/2022 | Wardle | A61F 9/00781 |
| 2022/0133538 A1* | 5/2022 | Pinchuk | A61F 9/0008 |
| | | | 604/8 |

OTHER PUBLICATIONS

Written Opinion of the International Searching Authority for PCT/CA2020/051358 dated Jan. 18, 2021.

* cited by examiner

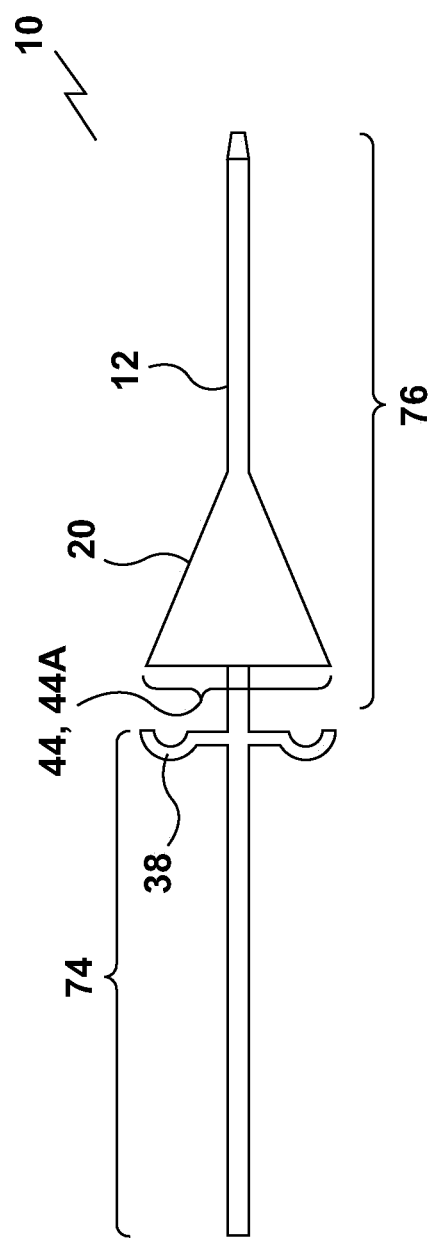
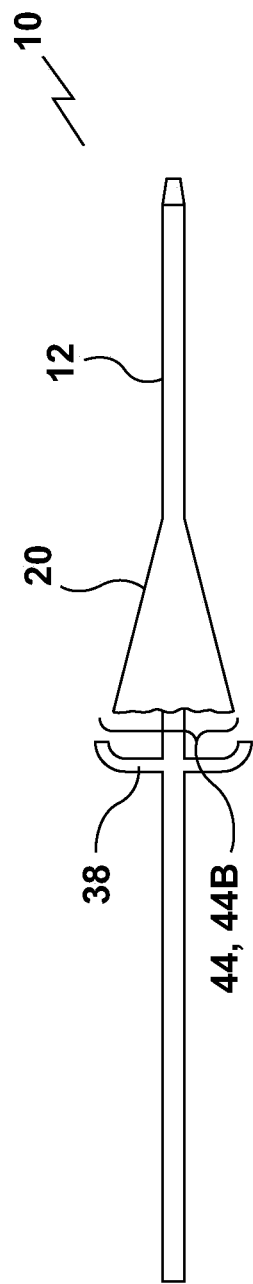
FIG. 1A
FIG. 1B

GLAUCOMA SHUNTS AND RELATED METHODS OF USE

CROSS REFERENCE TO RELATED APPLICATIONS

This application is a U.S. National Stage of International Application No. PCT/CA2020/051358, filed Oct. 9, 2020, which claims priority to Canadian Application No. 3,058,571, filed Oct. 11, 2019, the entire contents of each of which are fully incorporated herein by reference.

FIELD OF INVENTION

The present invention relates to glaucoma shunts. More specifically, the present invention relates to minimally invasive glaucoma surgery shunts.

BACKGROUND OF THE INVENTION

Glaucoma is a medical term describing a group of progressive optic neuropathies characterized by degeneration of retinal ganglion cells and retinal nerve fibre layer and resulting in changes in the optic nerve head. Glaucoma is a leading cause of irreversible vision loss worldwide. With the aging population, it is expected that the prevalence of glaucoma will continue to increase. Despite recent advances in imaging and visual field-testing techniques that allow the establishment of earlier diagnosis and treatment initiation, significant numbers of glaucoma patients are undiagnosed and present late in the course of their disease. This can lead to irreversible vision loss, reduced quality of life, and a higher socioeconomic burden.

Glaucoma may be categorized as primary or secondary glaucoma. Primary glaucoma is often defined as glaucoma that develops due to an unknown cause, while secondary glaucoma may develop from a known cause, such as injury, cataract, tumour or diabetes. Primary or secondary glaucoma may also be classified as open angle or angle-closure. It is estimated that 64.3 million people worldwide have glaucoma, of which three-quarters are open-angle. Glaucoma, both open-angle and angle-closure, is the second leading cause of irreversible blindness worldwide, with approximately 8.4 million people becoming blind from the disease.

Glaucoma may have a significant impact on patients' quality of life, such as the ability to walk, drive or read. The psychological burden may increase with decreasing vision, along with a growing fear of blindness, social withdrawal, and depression. Measurable loss in quality of life and functionality may be observed even in the early stages of the disease and the impact increases as visual field (VF) loss progresses.

Current treatment or prevention includes prescription eye-drops, oral medications, laser treatment, surgery or a combination of any of these. There is a need in the art for a medical device that can treat or prevent glaucoma without the need for invasive surgery.

SUMMARY OF THE INVENTION

It is an object of the present invention to provide a shunt for minimally invasive glaucoma surgery which addresses at least some of the limitations of the prior art.

According to one aspect of the present invention, there is provided a glaucoma shunt comprising: an elongate body with an outer surface and an inner surface, the elongate body comprising an inner wall that defines a lumen spanning a length of the elongate body.

In one embodiment, the shunt further comprises an umbrella-shaped structure connected to and extending from the glaucoma shunt such that the umbrella-shaped structure abuts an inner wall of an eye when positioned in the eye.

In another embodiment, the shunt further comprises one or more anchors laterally extending away from the elongate body and spaced from the umbrella-shaped structure. The one or more anchors abut an outer surface of an eye when positioned in the eye.

In yet another embodiment, at least a portion of the inner surface comprises poly(methylmethacrylate), acrylic, silicone, polypropylene, Collamer™, or a combination thereof. In another embodiment, at least a portion of the umbrella-shaped structure comprises silicone, acrylic, polypropylene, Collamer™, or a combination thereof. In another embodiment, at least a portion of the outer surface comprises acrylic, silicone, polypropylene, Collamer™, or a combination thereof. In another embodiment, at least a portion of the one or more anchors comprises silicone, acrylic, polypropylene, Collamer™, or a combination thereof.

In yet another embodiment, the glaucoma shunt decreases intraocular pressure by drainage of aqueous humour via the lumen. Embodiments of the glaucoma shunt may be used to treat glaucoma, for example primary open angle glaucoma, secondary open angle glaucoma, mixed glaucoma, or juvenile glaucoma.

According to another aspect of the present invention, there is provided a glaucoma shunt comprising: an elongate body with an outer surface and an inner surface, the elongate body comprising an inner wall that defines a lumen spanning a length of the elongate body, wherein at least a portion of the inner surface comprises a first biocompatible material, and at least a portion of the outer surface comprises a second biocompatible material.

In some embodiments of the glaucoma shunt, the first biocompatible material is poly(methylmethacrylate) (PMMA), silicone, acrylic, hydrophobic acrylate, hydrophilic acrylate, COLLAMER™, or combinations thereof. In such embodiments of the glaucoma shunt and others, the second biocompatible material is poly(methylmethacrylate) (PMMA), silicone, acrylic, hydrophobic acrylate, hydrophilic acrylate, COLLAMER™, or combinations thereof.

According to another aspect of the present invention, there is provided a glaucoma shunt comprising: an elongate body with an outer surface and an inner surface, the elongate body comprising an inner wall that defines a lumen spanning a length of the elongate body, wherein at least a portion of the inner surface comprises poly(methylmethacrylate), and at least a portion of the outer surface comprises acrylic.

In another embodiment, the glaucoma shunt further comprises an umbrella-shaped structure connected to and extending from the glaucoma shunt such that the umbrella-shaped structure abuts an inner wall of an eye when positioned in the eye, and at least a portion of the umbrella-shaped structure comprises poly(methylmethacrylate) (PMMA), silicone, acrylic, hydrophobic acrylate, hydrophilic acrylate, COLLAMER™, or combinations thereof.

In yet another embodiment, the glaucoma shunt further comprises one or more anchors laterally extending away from the elongate body and spaced from the umbrella-shaped structure and at least a portion of the one or more anchors comprises poly(methylmethacrylate) (PMMA), silicone, acrylic, hydrophobic acrylate, hydrophilic acrylate, COLLAMER™, or combinations thereof.

According to another aspect of the present invention, there is provided a method of decreasing intraocular pressure in an eye, the method comprising: inserting at least a portion of a glaucoma shunt into an anterior chamber of the eye, the glaucoma shunt comprising: an elongate body with an outer surface and an inner surface, the elongate body comprising an inner wall that defines a lumen spanning a length of the elongate body; and draining aqueous humour from the anterior chamber through the lumen.

In another embodiment of the present invention, the shunt further comprises an umbrella-shaped structure connected to and extending from the glaucoma shunt such that the umbrella-shaped structure abuts an inner wall of an eye when positioned in the eye. In another embodiment, the glaucoma shunt further comprises one or more anchors laterally extending away from the elongate body and spaced from the umbrella-shaped structure.

In yet another embodiment of the present invention, the method further comprising abutting at least a portion of the umbrella-shaped structure to the eye. In a further embodiment, abutting comprises abutting against a part of the eye, such as a cornea, or an iridocorneal angle. In another embodiment, abutting comprises abutting a portion of the umbrella-shaped structure against an inner surface of the part of the eye, such as the cornea or the iridocorneal angle and abutting a portion of the anchor against an outer surface of the part of the eye, such as the cornea or the iridocorneal angle.

In a further embodiment of the present invention, inserting comprises inserting the umbrella-shaped structure of the glaucoma shunt into the anterior chamber of the eye. In another embodiment, inserting comprises inserting the portion of the glaucoma shunt into the eye with the aid of a slit lamp. In yet another embodiment, inserting comprises inserting the glaucoma shunt under a conjunctiva of the eye. In some embodiments, inserting comprises inserting the glaucoma shunt under a Tenon's capsule of the eye.

In an embodiment of the present invention, the umbrella prevents migration of the glaucoma shunt while draining. In another embodiment, the one or more anchors prevent migration of the glaucoma shunt while draining.

According to another aspect of the invention, there is provided use of a glaucoma shunt for decreasing intraocular pressure in an eye, the use comprising: insertion of at least a portion of the glaucoma shunt into an anterior chamber of the eye, the glaucoma shunt comprising: an elongate body with an outer surface and an inner surface, the elongate body comprising an inner wall that defines a lumen spanning a length of the elongate body; and drainage of the aqueous humour from the eye through the lumen.

In an embodiment of the present invention, the shunt further comprises an umbrella-shaped structure connected to and extending from the glaucoma shunt such that the umbrella-shaped structure abuts an inner wall of an eye when positioned in the eye. In some embodiments, the use further comprising abutment of at least a portion of the umbrella-shaped structure to the eye. The shunt further comprises one or more anchors laterally extending away from the elongate body and spaced from the umbrella-shaped structure.

In some embodiments, the glaucoma shunt is abutted against a cornea or iridocorneal angle of the eye. In further embodiments, a portion of the umbrella-shaped structure is for abutment against an inner surface of the cornea or iridocorneal angle of the eye and a portion of the anchor is for abutment against an outer surface of the cornea or iridocorneal angle.

In some embodiments, the umbrella-shaped structure of the glaucoma shunt is for insertion into the anterior chamber of the eye. In further embodiments, the portion of the glaucoma shunt is for insertion into the eye with the aid of a slit lamp. In yet another embodiment, the glaucoma shunt is for insertion under a conjunctiva of the eye. In an embodiment, the glaucoma shunt is for insertion under a Tenon's capsule of the eye. In some embodiments, the umbrella-shaped structure prevents migration of the glaucoma shunt after insertion. In one embodiment, the one or more anchors prevent migration of the glaucoma shunt after insertion.

According to another aspect of the invention, there is provided an injection device for delivering a payload into a part of the eye. In one embodiment, the injection device comprises a body with a front end and an opposing rear end, an adjustable head extending from the front end of the body, comprising an outer wall with a hinge portion, the outer wall defining an inner cavity and a terminal end for insertion into the part of the eye; and an actuator mounted to the body and connected to the adjustable head such that movement of the actuator from a first position to a second position delivers the pay-load into the part of the eye.

In another embodiment of the injection device, the actuator is connected to the adjustable head via one or more pads located within the inner cavity. In some embodiments, the one or more pads abut the payload within the adjustable head. The one or more pads may be connected to the actuator such that movement of the actuator from the first position to the second position moves the pads from a first pad position to a second pad position. Movement of the one or more pads to the second pad position may push the payload from the inner cavity to the part of the eye.

In further embodiments, the injection device comprises an inner needle mounted to the one or more pads. In some embodiments, the needle extends past the terminal end of the adjustable head when the one or more pads are in the second pad position. In further embodiments, at least a portion of the payload is within a gauge of the needle.

In some embodiments of the injection device, the actuator is a slider, button or roller.

In further embodiments of the injection device, the terminal end of the adjustable head defines one or more sharpened edges.

In even further embodiments of the injection device, the payload is the glaucoma shunt as described hereinabove. In some cases, the payload is a slow-release drug delivery system.

BRIEF DESCRIPTION OF THE DRAWINGS

These and other features of the invention will become more apparent from the following description in which reference is made to the appended drawings wherein:

FIG. 1A shows a side elevation view of an embodiment of the glaucoma shunt in the deployed configuration;

FIG. 1B shows a side elevation view of the glaucoma shunt of FIG. 1A in the collapsed configuration;

DETAILED DESCRIPTION

Figure 2:
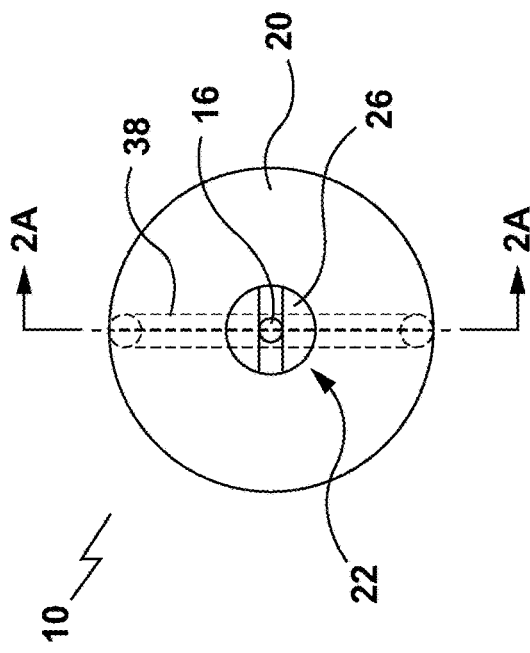
FIG. 2 shows a front end view of the glaucoma shunt of FIG. 1A.

One or more illustrative embodiments have been described by way of example. Described herein are glaucoma shunts and methods of treatment of glaucoma. All references to embodiments, examples, aspects, formulas, compounds, compositions, apparatuses, kits and the like are intended to be illustrative and non-limiting.

In one embodiment there is provided a glaucoma shunt 10 for decreasing intraocular pressure in an eye. Shunt 10 comprises an elongate body 12 with an outer surface 14 and an inner surface 16. Shunt 10 comprises an inner wall 17 that defines lumen 18. The lumen 18 spans a length of elongate body 12. Shunt 10 may comprise umbrella-shaped structure 20 mounted on and extending from shunt 10. The umbrella-shaped structure 20 abuts an inner wall of the eye when positioned in the eye.

Glaucoma shunt 10 may be used to treat or prevent glaucoma, such as primary open angle glaucoma, secondary open angle glaucoma, juvenile glaucoma or mixed glaucoma. Without wishing to be bound by theory, shunt 10 may be used to treat glaucoma by decreasing intraocular pressure in the eye via drainage of aqueous humour through lumen 18.

Inner membrane wall 34 refers to an inward facing surface of a part of the eye, such as a surface facing the anterior chamber. In some embodiments, the inner membrane wall 34 refers to the inner wall of the cornea, sclera, iridocorneal angle, or a combination thereof. Outer membrane surface 36 refers to an outer surface of a part of the eye, such as an outward facing surface (i.e. away from the anterior chamber) of the cornea, sclera, iridocorneal angle or a combination thereof. In some cases, the outer surface refers to parts of the conjunctiva or Tenon's capsule.

Referring to FIGS. 1 and 2, elongate body 12 comprises a head 22 and an opposed tail 24. Head 22 may define a suitably pointed shape with one or more slanted surfaces 26. Lumen 18 may extend through the elongate body 12 from head 22 to tail 24. Lumen 18 may be defined by inner surface 16. Lumen 18 may be free of any valves or obstructions to allow passive drainage of fluid, such as aqueous humour, from the eye. In some cases, lumen 18 and diameter 72 may be varied to modify the flow rate of aqueous humour through lumen 18 in use.

Figure 2A:
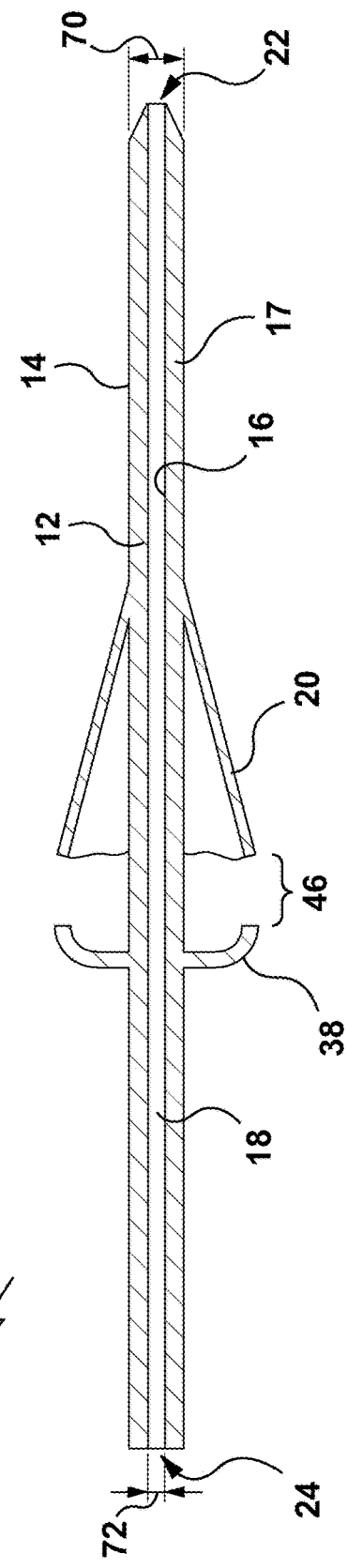
FIG. 2A shows a cross-sectional view taken along the 2A-2A cross-section line in FIG. 2.

Referring to FIGS. 1A, 1B and 2A, umbrella-shaped structure 20 can move between deployed and collapsed configurations. Umbrella-shaped structure 20 may be mounted on, or be integrated with, elongate body 12. Umbrella-shaped structure 20 may extend in a direction substantially away from head 22 and toward tail 24. Umbrella-shaped structure 20 has a suitable shape, such as a frustoconical shape and others. Migration of the glaucoma shunt 10 may be prevented by umbrella-shaped structure 20 when positioned in the eye. In example of a collapsed configuration of umbrella-shaped structure 20 is depicted in FIG. 1B and an example of a deployed configuration of umbrella-shaped structure 20 is depicted in FIG. 1A. In the deployed configuration, width 44A of the umbrella-shaped structure 20 may be greater than width 44B of the umbrella-shaped structure in the collapsed configuration. The collapsed configuration may be used during insertion into the eye of the patient. The umbrella-shaped structure 20 may then be deployed when it reaches anterior chamber 30. Deployed umbrella-shaped structure 20 may then engage the inner membrane wall 34 and prevent migration of the umbrella-shaped structure, relative to the eye. In some cases, umbrella-shaped structure 20 may transition between the collapsed and deployed configurations by mechanical means, such as a lever or switch. In other cases, umbrella-shaped structure 20 may transition between the configurations by a passive mechanism, such as elasticity of the umbrella-shaped structure, or free movement. Umbrella-shaped structure 20 may be stored in a collapsed configuration in an injector.

Figure 3:
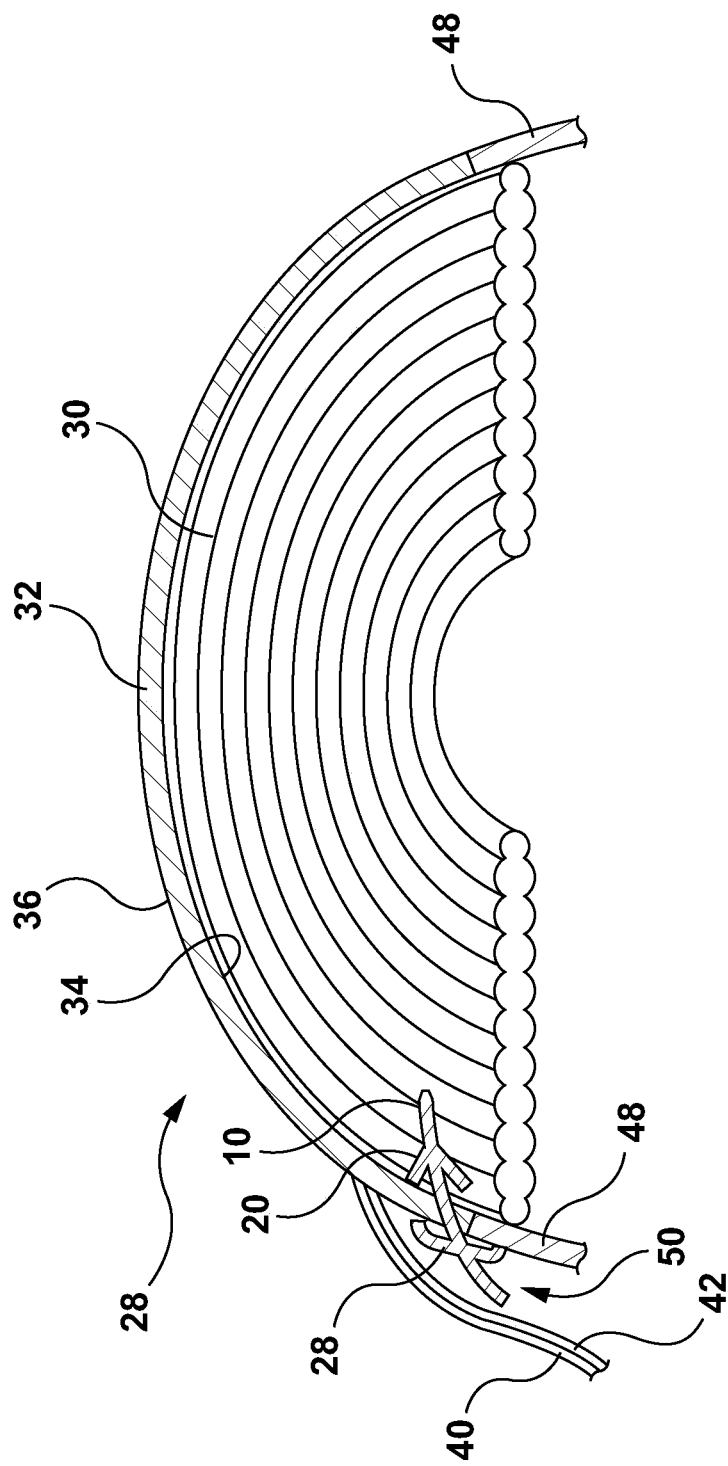
FIG. 3 shows a cross-sectional view of an eye and the glaucoma shunt of FIG. 1A.

Referring to FIG. 1, shunt 10 may comprise one or more anchors 38 extending away from, and substantially perpendicular to, the elongate body 12. Anchors 38 may be spaced from the umbrella-shaped structure 20 by width 46. For example, anchors 38 may be spaced from umbrella-shaped structure 20 so that a part of the eye, such as the width of cornea 32, may pass between anchors 38 and umbrella-shaped structure 20. In some cases, width 46 is sized to accommodate the diameter of the cornea 32 or the sclera 48 (FIG. 3). One or more anchors 38 may abut an outer membrane surface 36 of eye 28 in use. Migration of the glaucoma shunt 10 may be prevented by one or more anchors 38 in use. The shunt 10 may be locked in place relative to the eye by umbrella-shaped structure 20 and/or one or more anchors 38. In the embodiments pictured, anchors 38 are shaped as bars or hooks, but other suitable shapes may be used, such as ledges, steps, or other shapes.

Referring to FIGS. 1 and 3, in one embodiment there is described a method of decreasing intraocular pressure in an eye 28, the method comprising inserting at least a portion of glaucoma shunt 10 into an anterior chamber 30 of eye 28, abutting at least a portion of the umbrella-shaped structure 20 to an interior surface of eye 28. In some embodiments, the umbrella-shaped structure 20 and anchor 38 may act to "lock" the shunt in position relative to the eye and prevent migration of the shunt 10 relative to the eye. Shunt 10 drains the aqueous humour from the anterior chamber 30 via the lumen 18. Draining the aqueous humour may act to lower the intraocular pressure. The aqueous humour may drain into an appropriate subconjuctival area, such as a bleb 50 between the sclera and the Tenon's capsule or conjunctiva. In some cases, the aqueous humour is drained outside of the eye. The shunt 10 may be used to treat glaucoma, such as primary open angle or secondary open angle glaucoma by decreasing the intraocular pressure.

Referring to FIGS. 1 and 3, at least part of shunt 10 is inserted into the eye 28 in use. Shunt 10 may be inserted through the cornea 32 or iridocorneal angle into the anterior chamber 30. The anterior chamber may comprise aqueous humour, which may be drained through lumen 18 by passive means, such as diffusion. In certain embodiments, the shunt 10 may be inserted under the conjunctiva 40. In further embodiments, the shunt 10 may be inserted under the Tenon's capsule 42 and conjunctiva 40 and into the iridocorneal angle. Shunt 10 may be inserted such that the umbrella 20 is within the anterior chamber 30 of the eye.

Figure 4:
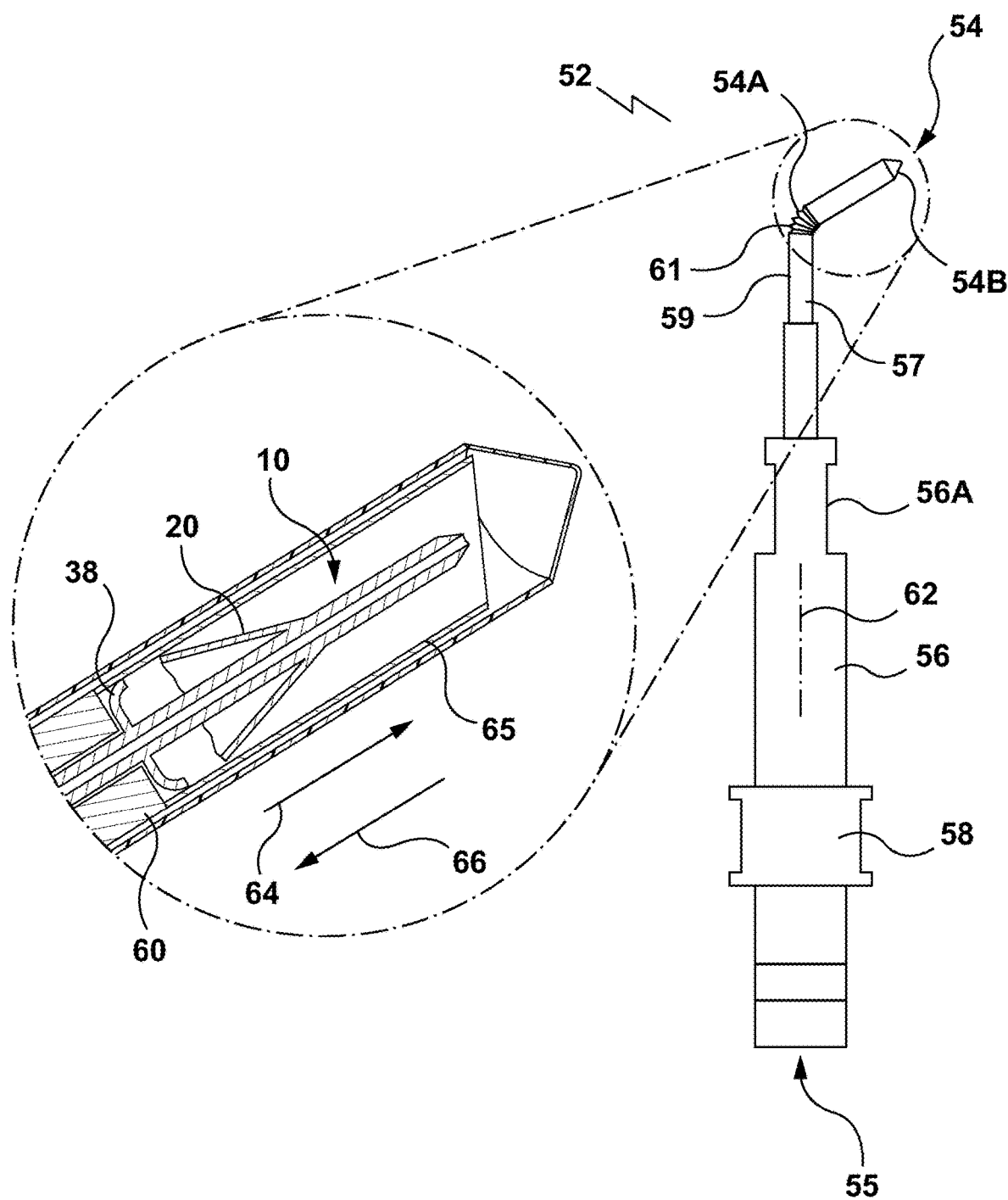
FIG. 4 shows a side elevation view of the glaucoma shunt of FIG. 1A with an embodiment of an injector.

Referring to FIGS. 3 and 4, insertion of shunt 10 may occur without the need for surgery. Shunt 10 may be inserted via an insertion device or injector 52, such as the embodiment shown in FIG. 4. Insertion device 52 comprises body 56, actuator 58, and an adjustable/flexible head 54. The adjustable head 54 extends from a front end 57 of the body 56. Body 56 may be shaped as a grip or handle to accommodate a user's hand.

A user of device 52 may position the flexible head 54 using the hinge portion 61 of the outer wall 59. The hinge portion 61 may comprise one or more hinges or joints, such as accordion hinge 54A. Hinge 54A may permit a right or left-handed user to operate the device. Other types of hinges known in the art may be used, such as living hinges and others. The hinge 54A may allow a user to bend the head 54 at a suitable angle, relative to a central axis 62 of body 56, such as 0-180° or) 0-(−180°.

Actuator 58 may be provided as a slider. Slider may be connected to pads 60 such that when the slider is moved along the axis 62, the pads move in a direction along head 54 substantially towards terminal end 54B, such as direction 64. Pads 60 may rest against anchor 38 and may act to grip the outer surface of shunt 10 to hold it in place relative to the device 52. One or more pads 60 may be connected to a needle 62. Needle 62 may be hollow, with the shunt 10 within the needle 62, and have a suitable shape with one or more sloped, sharpened edges. In some cases, needle 62 is shaped to correspond with terminal end 54B of head 54. Terminal end 54B may define one or more sharpened edges that are sharp enough to perforate part of the eye, such as the sub conjunctiva, Tenon's capsule, cornea, sclera and/or iridocorneal angle of the eye.

Actuator 58 may be provided as a push button (not pictured). The button may be connected to pads 60 such that when the button is depressed between a first and second position, the pads move in a direction along head 54 substantially towards terminal end 54B, such as direction 64. When the button is released from the second position to the first position, the pads may move in a direction substantially towards hinge 54A, such as direction 66. The first and second positions may be reversed such that depressing the button moves the pads in direction 66. The button may be positioned such that a user can operate the button with the user's thumb.

In another embodiment, actuator 58 may be provided as a roller (not pictured). The roller may be connected to pads 60 such that when the roller mechanism is moved from a first position to a second position, such as a right side to a left side (for a right-handed user), the pads move in a direction along head 54 substantially towards terminal end 54B, such as direction 64. When the roller is moved from the second position back to the first position, the pads may move in a direction substantially towards hinge 54A, such as direction 66. The first and second positions may be reversed for a left-handed user. The roller may move in a direction perpendicular to axis 62 in use.

The adjustable head 54 may be inserted into the eye, such as subconjunctival or under the Tenon's capsule. A user then operates the actuator 58, such as slider or a button, which is connected to operate one or more pads 60. When the head 54 is in position (i.e. under the conjunctiva but before breaching the outer wall of the eye) the user may operate the actuator 58. The actuator 58 may move pads 60 and needle 62 through the outer wall of the eye (such as the cornea and/or sclera). When the actuator 58 has moved from a first position, such as a rear 55 of the device in cases of a slider, to a second position, such as indentation 56A, the pads 60 may disengage from the payload, such as shunt 10. Once the pads 60 have disengaged, the actuator 58 may be moved back from the second position to the first position, thereby causing the pads 60 and needle 62 to move in a direction away from the eye, such as direction 66. The device 52 may be removed, leaving the payload, such as shunt 10, in the eye.

Insertion of glaucoma shunt 10 may occur with the aid of a slit lamp or surgical microscope. In some cases, shunt 10 is inserted ab externo or ab interno.

Referring to FIG. 3, shunt 10 may abut against cornea 32, such as in the anterior chamber, of eye 28. Umbrella-shaped structure 20 may abut against an inner membrane surface 34 of cornea 32 after insertion. The shunt 10 may pass through the iridocorneal angle, in use. The iridocorneal angle may be understood as an angular recess between the cornea and the anterior surface of the attached margin of the iris. Anchor 38 may abut against an outer membrane surface 36 of cornea 32, such as under tenon's capsule at the limbus external to cornea. Contacting or abutting the inner membrane surface 34 and/or outer membrane surface 36 may decrease migration of shunt 10 relative to eye 28.

At least one or more portions of shunt 10 may comprise one or more biocompatible materials. In some embodiments, all of shunt 10 may comprise one or more biocompatible materials. Examples of suitable material include poly(methylmethacrylate) (PMMA), silicone, acrylic, hydrophobic acrylate, hydrophilic acrylate, COLLAMER™ and others. In some cases, at least a portion of the inner surface 16 comprises PMMA. Inner surface 16 may be comprised entirely of PMMA. A portion of the first end 22, such as the tip of the shunt and slanted surfaces 26, may comprise PMMA. All or at least a portion of the umbrella-shaped structure 20 may comprise silicone. All or at least a portion of the outer surface 14 may comprise acrylic. All or at least a portion of the one or more anchors 38 may comprise silicone.

In some embodiments, a front portion 76 comprising the first end 22 and umbrella-shaped structure 20 may comprise a first biocompatible material, such as poly(methylmethacrylate) (PMMA), silicone, acrylic, hydrophobic acrylate, hydrophilic acrylate, COLLAMER™, or combinations thereof. In such embodiments and others, a back portion 74 comprises a second biocompatible material, such as poly (methylmethacrylate) (PMMA), silicone, acrylic, hydrophobic acrylate, hydrophilic acrylate, COLLAMER™ or combinations thereof. Front portion 76 may be a portion that is inserted into the eye in use. Back portion 74 may be a portion that is located in the sub conjunctival area in use. In a preferred embodiment, the front portion 76 comprises silicone as the first biocompatible material and the back portion 74 comprises acrylic.

Shunt 10 may be a microshunt. Shunt 10 may have a suitable length, such as about 1 to about 50 mm, such as 8 mm or 8.5 mm. Shunt 10 has have a suitable outer diameter 70, such as about 135 to about 400 μm, for example 165 μm or 170 μm. Shunt 10 has a suitable inner diameter 72, such as about 20 to about 305 μm, for example 50 μm. Shunt 10 may have a suitable width or spacing 46 between the umbrella-shaped structure 20 and anchor 38 to accommodate a part of the eye, such as the cornea or sclera. Spacing 46 may be a suitable width, such as about 0.3 to about 0.8 mm, for example 0.5 mm. The actual size of the shunt may be determined based on the application. For example, different inner diameters may be used to effect different flow rates through the lumen. In some cases, a narrower lumen will result in a slower rate of drainage from the anterior chamber.

Suitable lengths may include a range of about 0.1 to about 200 mm or any value therebetween (optionally rounded to the nearest 0.1), or any subrange spanning between any two of these values, such as 8.5 mm or 25.4 mm. For example, lengths of 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200 mm and others are considered.

Suitable inner diameters and outer diameters may include a range of about 0.1 to about 2000 µm or any value therebetween (optionally rounded to the nearest 0.1), or any subrange spanning between any two of these values, such as 135-195 µm or 20-80 µm. For example, diameters of 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200 µm and others are considered.

Shunt 10 may be used in combination with other suitable treatments. Some examples include cataract surgery, prescription eye-drops, oral medication, laser treatment, trabeculectomy, other shunts, surgery and others. Shunt 10 may be used in combination with metabolites such as MMC (mitomycin C), 5-FU (5-fluorouracil), Anti-Vascular Endothelial Growth Factor (AntiVEGF) treatments, such as Avastin/Lucentis/Eylea, and others.

Shunt 10 and/or injector 52 may be used for delivering drugs and/or drug delivery devices into the eye. For example, the payload within injector 52 may be a slow release drug delivery device. Suitable ocular drug delivery devices known in the art may be used, for example those described in Patel, A. et al. "Ocular drug delivery systems: An overview." *World journal of pharmacology* vol. 2, 2 (2013): 47-64, herein incorporated by reference. Shunt 10 may be used to deliver drugs into a part of the eye, for example through lumen 18.

In the event of conflicting information and statements between any reference referred to or incorporated herein and the present disclosure, the present disclosure will act as the guiding authority.

The present invention has been described with regard to one or more embodiments. However, it will be apparent to persons skilled in the art that a number of variations and modifications can be made without departing from the scope of the invention as defined in the claims.

What is claimed is:

1. An injection device for delivering a glaucoma shunt into a part of an eye, the injection device comprising:
   a body with a front end and an opposing rear end, the body extending along a first axis;
   an adjustable head connected to the front end of the body, the adjustable head comprising an outer wall defining an inner cavity, and secured to the front end of the body by an adjustable joint, wherein the adjustable head is adjustable via the adjustable joint to extend along a second axis, wherein the second axis forms an angle relative to the first axis, and wherein the angle of the adjustable head can be adjusted while the adjustable head remains connected to the front end of the body;
   an actuator connected to the adjustable head via an internal structure located within the inner cavity;
   a needle which is mounted to the internal structure, the needle being hollowed and extending along the second axis; and
   a glaucoma shunt stored within the hollow needle,
   wherein movement of the actuator from one position to another position causes the internal structure and the needle to move relatively to the adjustable head in a direction away from the eye, while the adjustable head and the needle remain on the second axis, leaving the glaucoma shunt in the part of the eye.

2. The injection device of claim 1, wherein the actuator is a slider, button, or roller.

3. The injection device of claim 2, wherein the actuator is positioned such that a user can operate the actuator with a finger.

4. The injection device of claim 1, wherein the glaucoma shunt comprises one or more biocompatible materials.

5. The injection device of claim 1, wherein the glaucoma shunt comprises an elongate body with an outer surface and an inner surface, the elongate body comprising an inner wall that defines a lumen spanning a length of the elongate body.

6. The injection device of claim 5, wherein the elongate body comprises a head and an opposed tail, wherein the lumen extends through the elongate body from head to tail.

7. The injection device of claim 5, wherein the glaucoma shunt includes one or more anchors extending away from the elongate body configured, in use, to abut an outer membrane surface of the eye and prevent migration of the glaucoma shunt.

8. The injection device of claim 1, wherein the body is shaped as a grip or handle to accommodate a user's hand.

9. The injection device of claim 1, wherein the adjustable joint includes a hinge portion on the outer wall.

10. The injection device of claim 9, wherein the hinge portion includes one or more hinges or joints.

11. The injection device of claim 1, wherein the glaucoma shunt has an outer diameter from about 135 to about 400 µm.

12. The injection device of claim 1, wherein the glaucoma shunt has an inner diameter of from about 20 to about 305 µm.

13. The injection device of claim 1, wherein the internal structure includes one or more pads.

14. The device of claim 1, wherein the needle is housed within the inner cavity and is configured to move out of the inner cavity and extend past a terminal end of the adjustable head.

15. The device of claim 1, wherein the angle at the adjustable joint is selectively adjusted from 0 to 180° or 0 to −180°.

16. A method of decreasing intraocular pressure in an eye, comprising:
   providing an injection device including
   a body with a front end and an opposing rear end, the body extending along a first axis;
   an adjustable head connected to the front end of the body, the adjustable head comprising an outer wall defining an inner cavity, and secured to the front end of the body by an adjustable joint, wherein the adjustable head is adjustable via the adjustable joint to extend along a second axis, wherein the second axis forms an angle relative to the first axis, and wherein the angle of the adjustable head can be adjusted while the adjustable head remains connected to the front end of the body;

an actuator connected to the adjustable head via an internal structure located within the inner cavity;

a needle which is mounted to the internal structure, the needle being hollowed and extending along the second axis; and a glaucoma shunt stored within the hollow needle, adjusting the joint to position the adjustable head at said angle relative to the first axis;

positioning the head at a desired shunt insertion location against the eye;

inserting the needle into the eye; and moving the actuator from one position to another position causing the internal structure and the needle to move relative to the adjustable head and in a direction away from the eye, along the second axis, thereby leaving the glaucoma shunt in the eye.

17. The method of claim 16, wherein inserting the needle into the eye includes inserting under a Tenon's capsule of the eye or under a conjunctiva of the eye.

\* \* \* \* \*